(12) United States Patent
Shimoyama

(10) Patent No.: US 9,492,298 B2
(45) Date of Patent: Nov. 15, 2016

(54) STENT DELIVERY SYSTEM

(71) Applicant: TERUMO KABUSHIKI KAISHA, Shibuya-ku (JP)

(72) Inventor: Masakazu Shimoyama, Ashigarakami-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 69 days.

(21) Appl. No.: 14/447,767

(22) Filed: Jul. 31, 2014

(65) Prior Publication Data

US 2014/0343660 A1    Nov. 20, 2014

Related U.S. Application Data

(63) Continuation of application No. PCT/JP2013/052726, filed on Feb. 6, 2013.

(30) Foreign Application Priority Data

Feb. 28, 2012    (JP) .................. 2012-040817

(51) Int. Cl.
    *A61F 2/06*      (2013.01)
    *A61F 2/966*      (2013.01)
    *A61F 2/82*      (2013.01)
    *A61F 2/95*      (2013.01)

(52) U.S. Cl.
    CPC ............ *A61F 2/966* (2013.01); *A61F 2/82* (2013.01); *A61F 2002/9517* (2013.01); *A61F 2250/0073* (2013.01)

(58) Field of Classification Search
    CPC .. A61F 2002/9517; A61F 2/966; A61F 2/95; A61F 2/2436; A61F 2/962; A61F 2002/9534; A61F 2002/9665; A61F 2/2466; A61F 2/954; A61B 17/00234

USPC ....... 606/108, 191, 194, 198, 200; 623/1.11, 623/1.12, 2.11

See application file for complete search history.

(56) References Cited

U.S. PATENT DOCUMENTS

2005/0273151 A1    12/2005    Fulkerson et al.

FOREIGN PATENT DOCUMENTS

| | | |
|---|---|---|
| JP | 2007-504897 A | 3/2007 |
| JP | 2008-501442 A | 1/2008 |
| JP | 2011-194068 A | 10/2011 |
| WO | WO 2005/032614 A2 | 4/2005 |
| WO | WO 2011/122444 A1 | 10/2011 |

OTHER PUBLICATIONS

International Search Report (PCT/ISA/210) mailed on May 14, 2013, by the Japanese Patent Office as the International Searching Authority for International Application No. PCT/JP2013/052726.

*Primary Examiner* — Katherine M Shi
(74) *Attorney, Agent, or Firm* — Buchanan Ingersoll & Rooney PC

(57) ABSTRACT

An operating unit in a stent delivery system comprises a displacement body including a first body connected to an outer tube body and a second body which is connected to the first body and meshed with a rotary roller. A first connection surface of the first body is formed with a first convex portion and a first concave portion recessed relative to the first convex portion. The first convex portion engages a second concave portion of the second body and a second convex portion engages the first concave portion. When movement of the displacement body becomes difficult for some reason and the operator forcibly rotates the rotary roller, the engaged state of the second body and the first body is released and the second body is relatively moved, thus preventing movement of the first body in the axial direction.

20 Claims, 6 Drawing Sheets

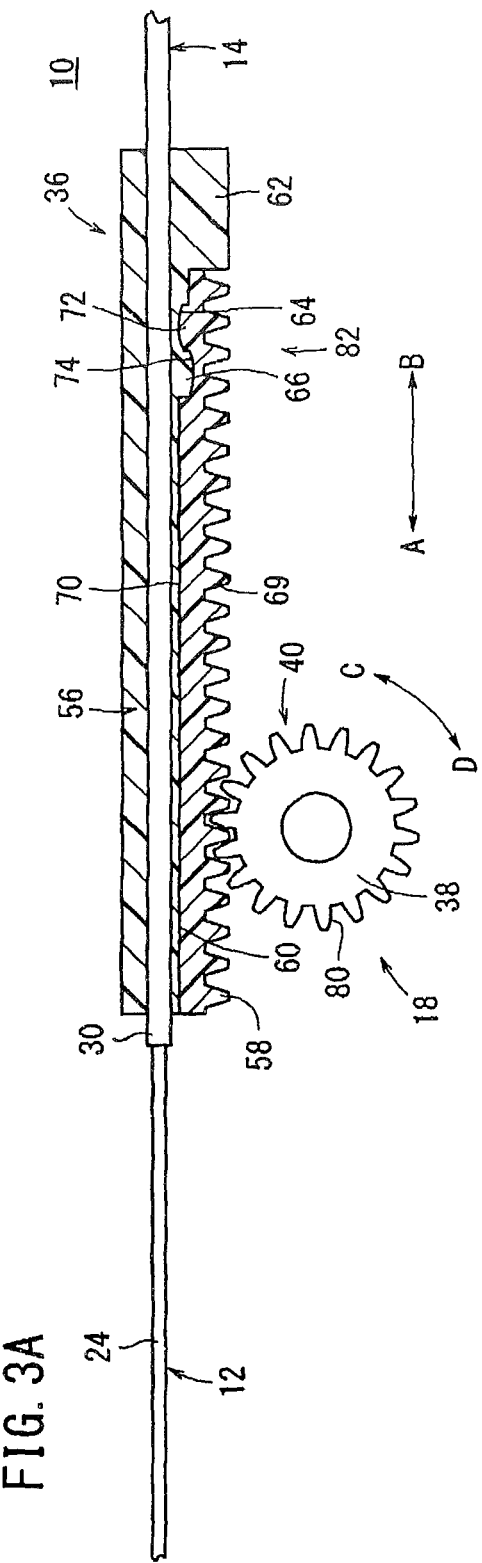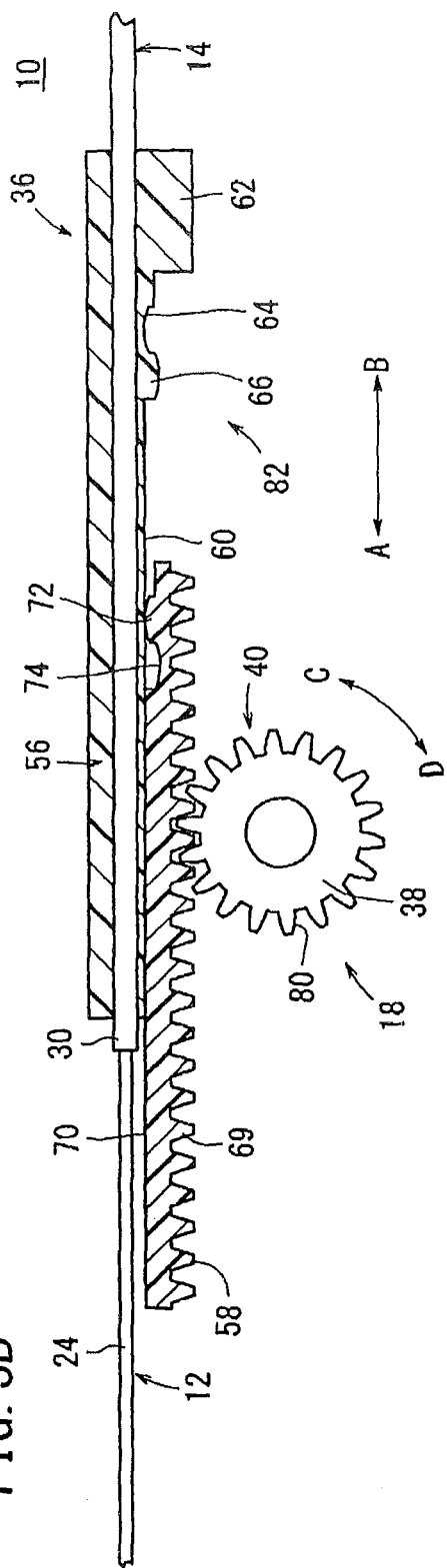

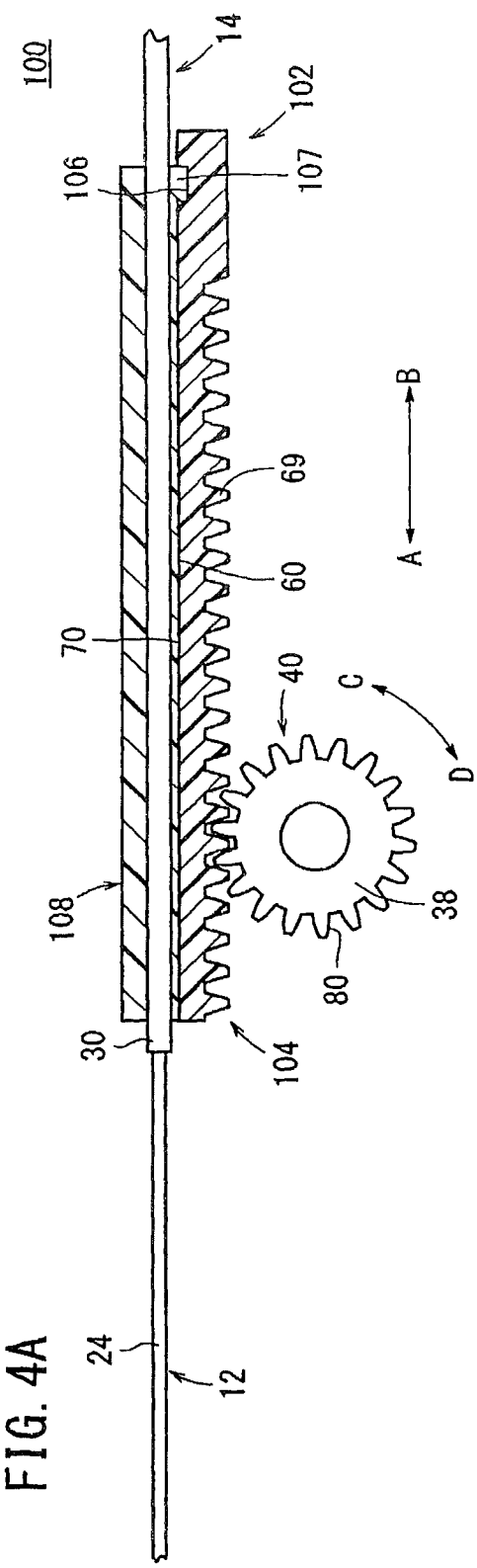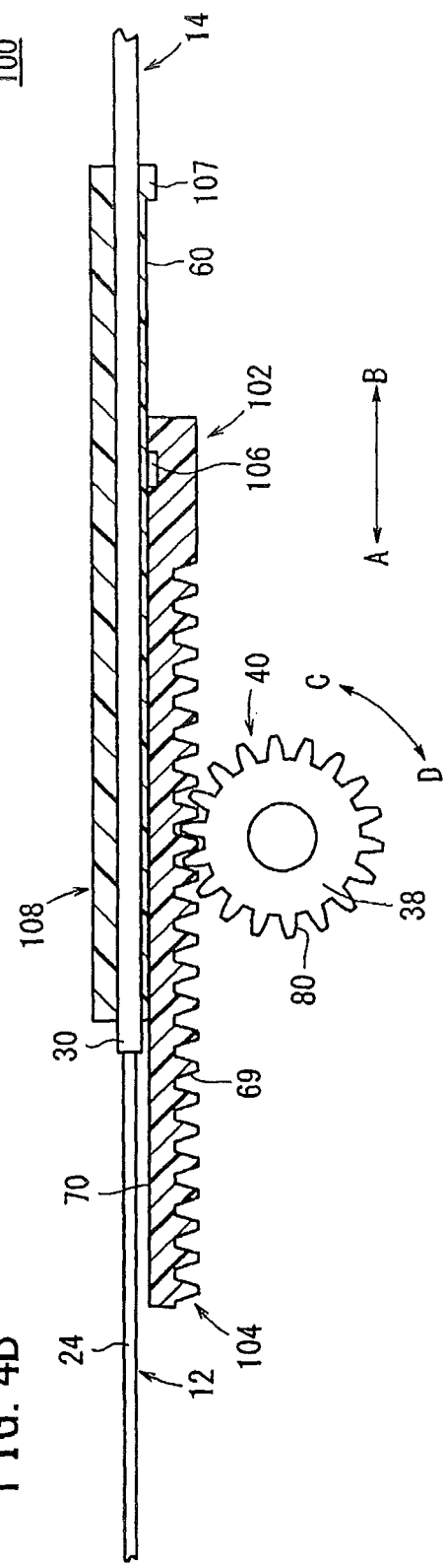
FIG. 4A
FIG. 4B

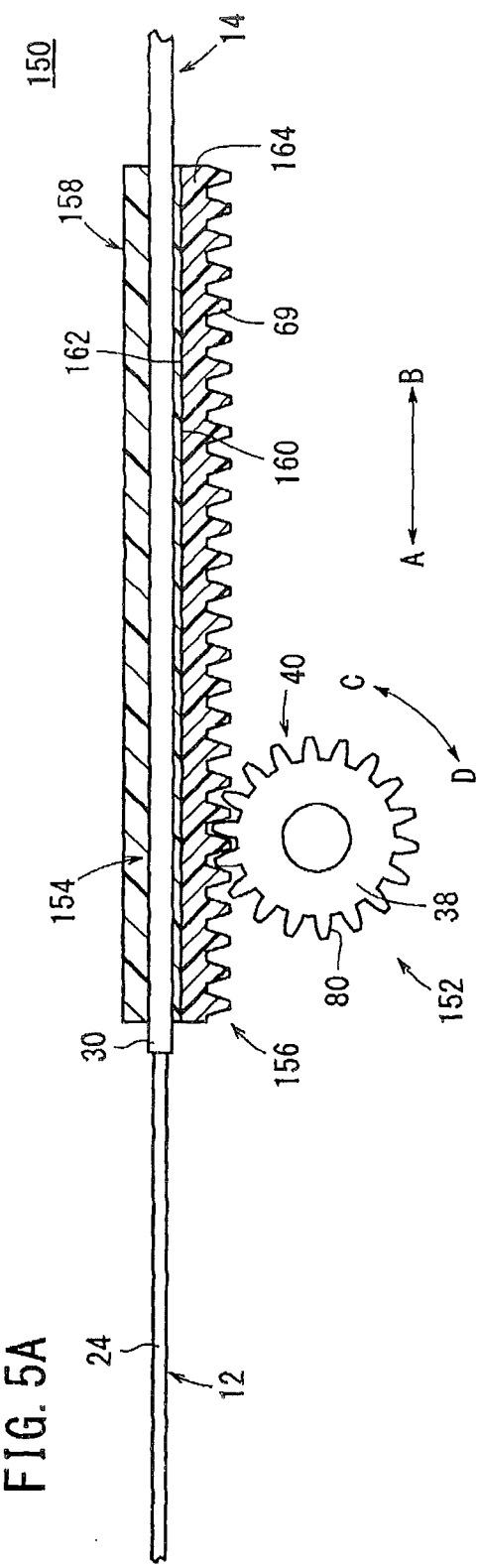
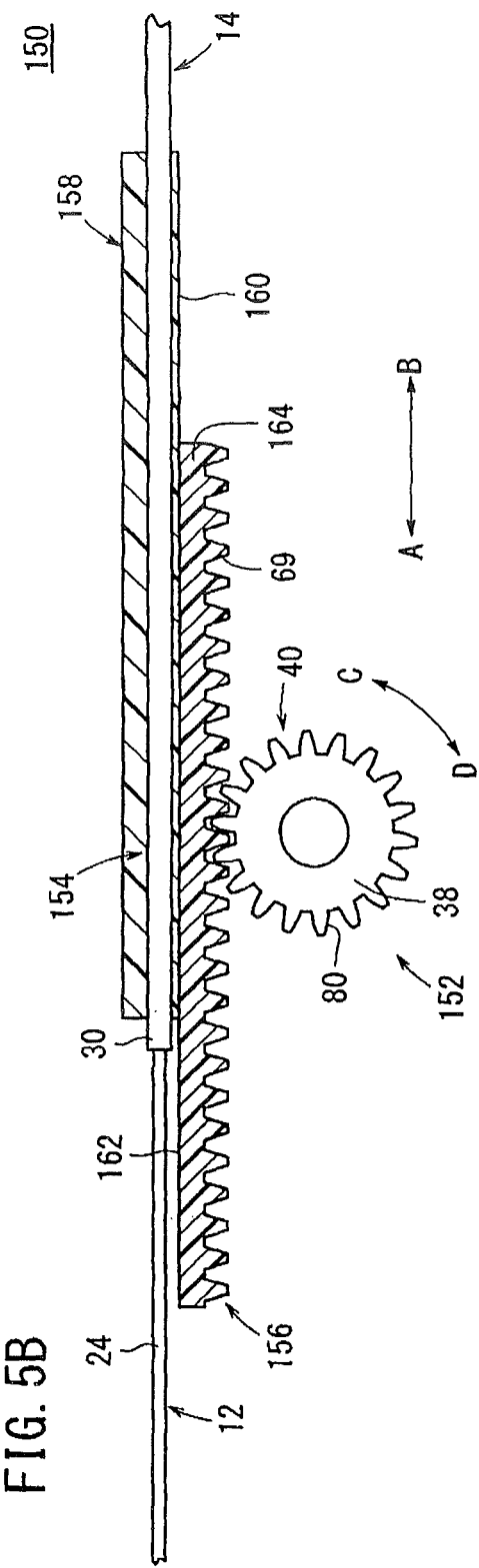

STENT DELIVERY SYSTEM

CROSS REFERENCES TO RELATED APPLICATIONS

This application is a continuation of International Application No. PCT/JP2013/052726 filed on Feb. 6, 2013, and claims priority to Japanese Application No. 2012-040817 filed on Feb. 28, 2012, the entire content of both of which is incorporated herein by reference.

TECHNICAL FIELD

The present invention generally relates to a stent delivery system for delivering and indwelling a stent into a lumen of a living body such as a blood vessel.

BACKGROUND DISCUSSION

Conventionally, there have been cases where a stent, which is formed in the shape of a hollow cylinder having a multiplicity of openings in its side wall from a metallic wire or the like, to be expanded in a lumen of a living body, such as a blood vessel, bile duct, trachea, esophagus and urethra, is used for improvement of a stenosed part or an obstructed part generated in the lumen of the living body.

In connection with the case of a self-expandable stent in which the stent itself has a self-expanding function, for example, there has been known a stent delivery system in which the stent is delivered into a lumen of a living body in the state of being compressed and contained in a gap between an inner tube and an outer tube, and then the outer tube is retracted proximally so as to release the stent, whereby the stent is put indwelling in a desired part in the lumen.

As disclosed in Japanese Application Publication No. 2007-504897, for example, the above-mentioned stent delivery system has an operating mechanism for moving the outer tube in an axial direction relative to the inner tube. In the operating mechanism, a gear rack is meshed with a gear of a rotatable wheel, and the outer tube is configured to be connected to an end portion of the gear rack. With the wheel rotated in a predetermined direction, the gear rack is advanced and retracted in the axial direction so as to move the outer tube relative to the inner tube, whereby the stent is released to the exterior of the outer tube.

SUMMARY

In the stent delivery system having the operating mechanism as described above, the gear rack and the outer tube connected to the gear rack can be moved in the axial direction along with the rotation of the wheel. Therefore, in the case where the outer tube is caught in the lesion in a lumen of a living body or the like so that movement of the outer tube in the axial direction is made difficult, for example, if an operator continues to forcibly rotate the wheel, the gear rack and the outer tube are forcibly pulled in the axial direction. This is accompanied by exertion of an excessive load on the stent delivery system (especially, on the outer tube). As a result, the stent delivery system might be broken, so that a broken component part of the stent delivery system may be left in the lumen of the living body.

The stent delivery system disclosed here is configured so that breakage due to exertion of an excessive load when movement of the outer tube becomes difficult can be prevented from occurring.

According to one aspect disclosed here, a stent delivery system includes: an inner tube; a stent which is compressed toward a center axis and disposed on a distal side of the inner tube at a time of insertion into a lumen of a living body, and which is restored to its pre-compression shape by expanding outward when put indwelling in the lumen of the living body; an outer tube disposed on an outer surface side of the inner tube and possessing a lumen containing the stent, the outer tube being axially movable in a proximal direction relative to the inner tube to release the stent to an exterior of the stent delivery system; and an operating unit operatively connected to the outer tube to axially move the outer tube relative to the inner tube. The operating unit comprises a housing, an operation body operable by an operator, a displacement body which is mounted in the housing to axially move relative to the housing. The displacement body includes a first block connected to the outer tube and a second block on which a load is exerted due to operation of the operation body by the operator, with the second block being connected to the first block. Furthermore, the operating unit comprises a releasing mechanism by which the connection between the first block and the second block is released so that the second block is moved relative to the first block when a load of not less than a predetermined value is applied to the second block from the operation body.

Even in a case where the movement of the displacement body and the outer tube connected to the displacement body in the axial direction becomes difficult for some reason and the operator forcibly operates the operation body, with the exertion of the load of not less than the predetermined value on the second block of the displacement body, the connection between the first block and the second block is released due to the releasing mechanism and the second block is relatively moved relative to the first block, whereby it is possible to prevent the transmission of the load to the first block. Therefore, the outer tube connected to the first block is prevented from being forcibly pulled in the axial direction. As a result, breakage of each member constituting the stent delivery system due to the exertion of the excessive load is reliably prevented.

According to another aspect, a stent delivery system comprises: an outer tube possessing a lumen and an inner surface; an inner tube possessing an outer surface, with the inner tube being positioned in the lumen of the outer tube so that an annular space exists between the outer surface of the inner tube and the inner surface of the outer tube; an operating unit operable by a user to axially move the outer tube in a proximal direction relative to the inner tube; and a stent positioned in the annular space between the outer surface of the inner tube and the inner surface of the outer tube. The stent is positioned at a distal end portion of the inner tube and is compressed radially inwardly, and is outwardly expandable exterior of the stent delivery system to be positioned in a lumen of a living body when the outer tube is axially moved in the proximal direction relative to the inner tube. The operating unit comprises: a housing; an operation body mounted on the housing and operable by an operator; a first block connected to the outer tube so that axial movement of the first block results in the axial movement of the outer tube relative to the inner tube; and a second block connected to the operation body so that operation of the operation body axially moves the second block. The first block and the second block are connected to each other by a releasable connection that maintains the connection between the first and second blocks when a load less than a predetermined value is applied to the second block by the operation of the operation body to transfer axial movement of the second block resulting from the operation of the operation body to the first block to axially move the first block, and that releases the connection between the first and second blocks when a load not less than a predetermined value is applied to the second block by the operation of the operation body so that axial movement of the second block resulting from the operation of the operation body is not transferred to the first block.

According to a further aspect, a method comprises: positioning a distal end of a stent delivery system in a lumen of a living body, wherein the stent delivery system comprises an outer tube, an inner tube positioned in the outer tube, an inwardly compressed stent between an outer surface of the inner tube and an inner surface of the outer tube, an operation body that is operable by an operator, a first block connected to the outer tube, and a second block connected to the operation body, with the second block being connected to the first block. The method further includes operating the operation body to axially move the second block in a proximal direction while the distal end of the stent delivery system is in the lumen of the living body, and transferring the axial movement of the second block to the first block by maintaining the connection between the second block and the first block when a load less than a predetermined value is applied to the second block by the operation of the operation body to axially move the first block in a proximal direction, with the axial movement of the first block in the proximal direction causing the outer tube to axially move in the proximal direction relative to the inner tube to uncover the stent and allow the stent to outwardly expand in the lumen of the living body. The method further involves not transferring the axial movement of the second block to the first block by releasing the connection between the second block and the first block when a load not less than a predetermined value is applied to the second block by the operation of the operation body so that the axial movement of the second block does not result in axial movement of first block.

BRIEF DESCRIPTION OF DRAWINGS

FIG. 3A is a partially omitted enlarged view showing the vicinity of a rotary roller and a displacement body shown in FIG. 2, and FIG. 3B is an enlarged view showing a state where a second body of the displacement body shown in FIG. 3A is disengaged from the first body and is moved toward a proximal side.

FIG. 4A is a partially omitted enlarged view showing the vicinity of a rotary roller and a displacement body of an operating unit provided with a releasing mechanism according to a modified example, and FIG. 4B is an enlarged view showing a state where a second body of the displacement body shown in FIG. 4A is disengaged from the first body and is moved toward a proximal side.

FIG. 5A is a partially omitted enlarged view showing the vicinity of a rotary roller and a displacement body in a stent delivery system according to a second embodiment representing another example of the stent delivery system disclosed here, and FIG. 5B is an enlarged view showing a state where a second body of the displacement body shown in FIG. 5A is disengaged from the first body and is moved toward a proximal side.

DETAILED DESCRIPTION

Figure 1:
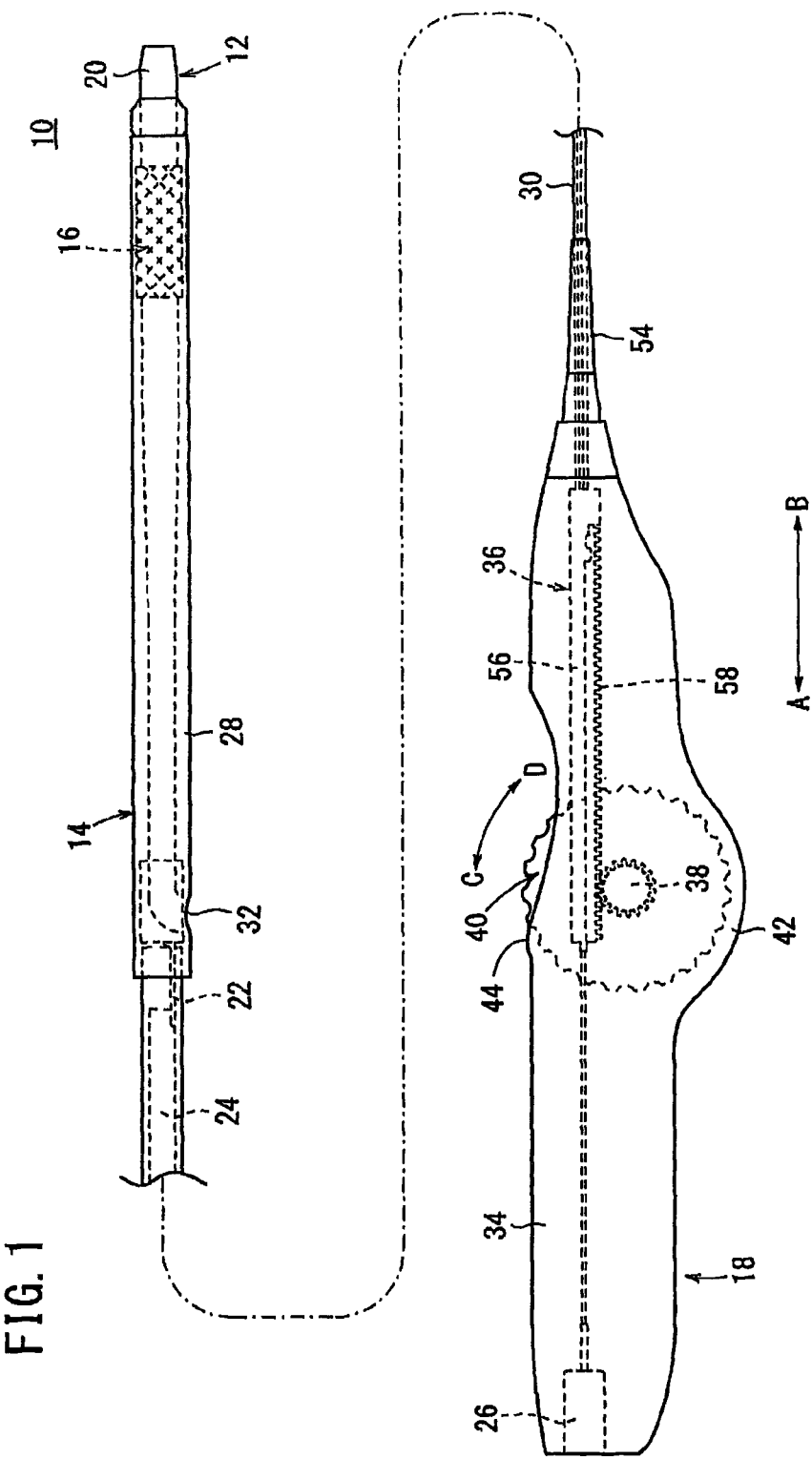
FIG. 1 is a side view of a stent delivery system according to a first embodiment representing an example of the stent delivery system disclosed here.

As shown in FIG. 1, illustrating an example of the stent delivery system disclosed here, the stent delivery system 10 includes: an inner tube body (inner tube) 12 formed in a tubular shape; an outer tube body (outer tube) 14 disposed on the outer circumference side of the inner tube body 12 (the inner tube is positioned in a lumen in the outer tube); an expandable stent 16 contained between the inner tube body 12 and the outer tube body 14; and an operating unit 18 for moving the outer tube body 14 relative to the inner tube body 12.

In FIG. 1, the left side of the inner tube body 12 and the outer tube body 14 is referred to as the "proximal end (rear end)" side (direction of arrow A), and the right side of the inner tube body 12 and the outer tube body 14 is referred to as the "distal end" side (direction of arrow B), the same applying also to the other figures.

As shown in FIG. 1, the inner tube body 12 includes: a first distal tube 20 in which is disposed a guide wire lumen into which a guide wire is inserted and passes through; a first proximal tube 24 connected through a connecting member 22 to the proximal side or proximal end (the direction of arrow A) of the first distal tube 20; and a connector 26 connected to the proximal end of the first proximal tube 24.

This inner tube body 12 is composed of the tubular bodies, in which the distal ends and proximal ends of both the first distal tube 20 and the first proximal tube 24 are respectively open, and the distal end of the first distal tube 20 protrudes distally beyond the distal end of the outer tube body 14. The above-mentioned guide wire is used, for example, for guiding the stent delivery system 10 to a lesion in a lumen of a living body.

The inner tube body 12 is configured such that the proximal end of the first distal tube 20 and the distal end of the first proximal tube 24 are connected to each other through the connecting member 22 inside the outer tube body 14. In addition, the first proximal tube 24 has a lumen penetrating through first proximal tube 24 from the distal end to the proximal end of first proximal tube 24. A liquid such as physiological saline is injected into the lumen of first proximal tube 24 via the connector 26.

The outer tube body 14 is composed of tubular bodies. The tubular bodies constituting the outer tube body 14 include a second distal tube 28 in which the first distal tube 20 of the inner tube body 12 is disposed and a second proximal tube 30 which is connected to the proximal end side (the direction of arrow A) of the second distal tube 28 and in which the first proximal tube 24 is disposed. The distal end of the second distal tube 28 functions as a release port at the time of indwelling the stent 16 into a lesion of a lumen of a living body, and functions also as a containing port at the time of once again containing the stent 16 having been released to an intermediate extent.

The proximal end of the second distal tube 28 includes a guide wire leading-out hole 32 which opens exterior of the stent delivery system to establish communication between the inner lumen of the second distal tube 28 and the exterior. The guide wire leading-out hole communicates with the opening of the guide wire lumen of the first distal tube 20 positioned inside the second distal tube. Through the guide wire leading-out hole 32, the guide wire is inserted into and passes through the guide wire lumen of the inner tube body 12.

The stent 16 possesses the shape of a substantially cylindrical mesh having a multiplicity of openings. The stent 16 is a self-expandable stent which is disposed between the second distal tube 28 of the outer tube body 14 and the first distal tube 20 of the inner tube body 12. That is, the stent 16 is located in an annular space between the outer surface of the first distal tube 20 (inner tube) and the inner surface of the second distal tube 28 (outer tube). The stent 16 is located in the space while the stent is compressed radially inward toward the center axis at the time of insertion into a lumen of a living body, and which, by being released via the distal end of the outer tube body 14 into a lesion in the lumen of the living body, automatically expands radially outward to be restored to its pre-compression expanded shape.

Figure 2:
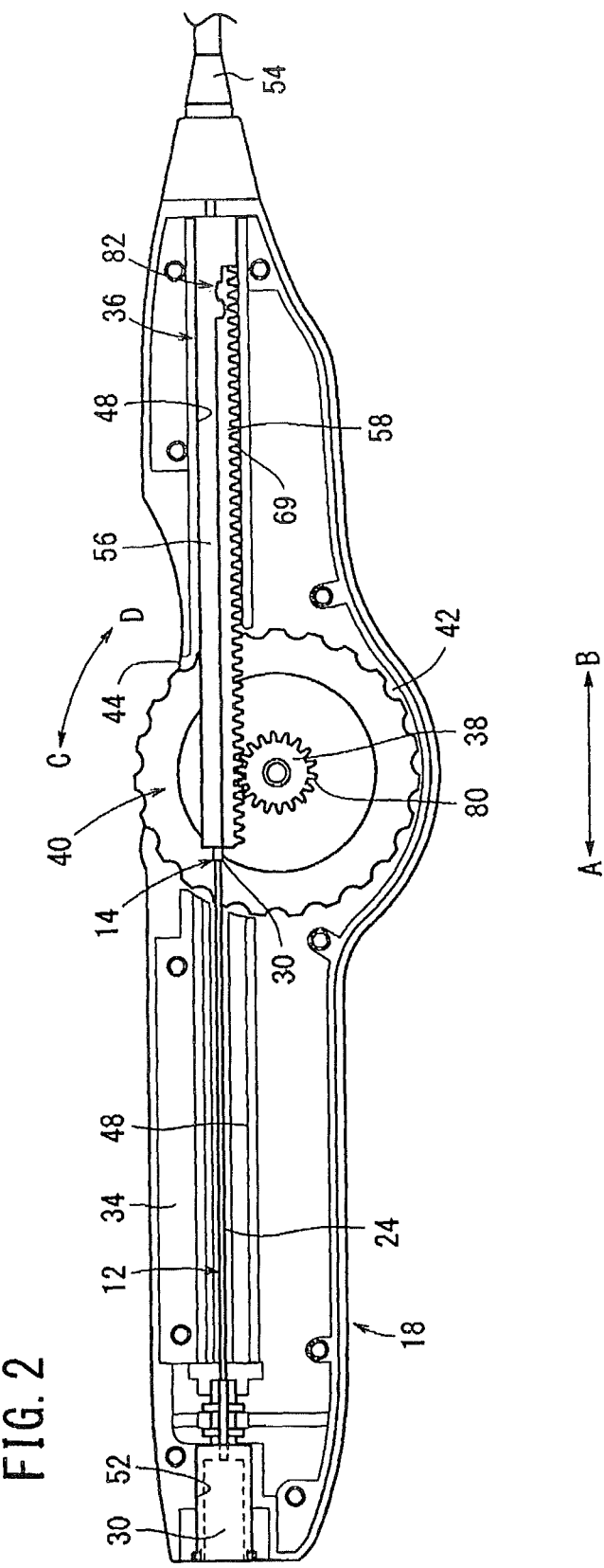
FIG. 2 is a side view of the inside of an operating unit of the stent delivery system shown in FIG. 1.

As shown in FIGS. 1 and 2, the operating unit 18 includes: a housing 34; a displacement body 36 contained inside the housing 34 and connected to the outer tube body 14; and a rotary roller (operation body) 40 which rectilinearly moves the displacement body 36 and has a gear 38 meshed with a second tooth portion 69 to be described later, and is operated by the operator.

The housing 34 is round-shaped at its substantially central portion. A roller containing section 42 configured to contain the rotary roller 40 is formed in the substantially central portion of the housing. Part of the rotary roller 40 is exposed to the exterior through a roller hole 44 formed in the roller containing section 42.

In addition, the rotary roller 40 is rotatably supported by a pair of bearings formed at inner wall of the housing 34.

The inside of the housing 34 is formed with a set of containing grooves 48 in which the displacement body 36 is contained and retained so as to be movable in the axial direction (in the directions of arrows A and B).

A connector containing section 52 which contains the connector 26 is formed on the proximal end side (the direction of arrow A) relative to the containing groove 48. The connector 26 is fixed to the housing 34 by being contained in the connector containing section 52. As a result, the proximal end of the first proximal tube 24 constituting the inner tube body 12 is fixed to the operating unit 18 through the connector 26.

Meanwhile, a tapered tip portion 54 by which the second proximal tube 30 of the outer tube body 14 is slidably retained is mounted on the distal end of the housing 34. That is, the second proximal tube 30 of the outer tube body 14 is slidable relative to the tapered tip portion 54. The tapered tip portion 54 includes a through-hole into which the second proximal tube 30 is inserted and through which the second proximal tube 30 passes.

As shown in FIGS. 1 to 3B, the displacement body 36 is composed of a set of members or bodies, namely first and second members or bodies 56 and 58. In the illustrated example, the members or bodies 56, 58 are elongated pieces or elements. In the illustrated embodiment, the first and second bodies 56 and 58 possess straight shapes. The proximal end of the second proximal tube 30 of the outer tube body 14 is fixed to the first body 56 so that the second proximal tube 30 and the first body 56 move together as a unit. In the illustrated embodiment, the first body 56 is positioned upward in the housing 34. That is, the first body 56 is positioned in the housing at a location upward (at least in part) relative to the second body 58.

The displacement body 36, composed of the first and second block bodies 56 and 58, is located in the containing groove 48 inside the housing 34, whereby the displacement body 36 is retained in the state of being rectilinearly movable toward the distal side and the proximal side (in the directions of arrows A and B) of the housing 34.

The first body 56 is provided with a first connection surface 60 extending in the moving direction (in the directions of arrows A and B) of the displacement body 36 on a surface of the second body 58 side (i.e., on the side of the first body 56 facing the second body 58). The first body 56 also includes a locking portion 62 at the distal end of the first body 56. The first connection surface 60 is planar-shaped and extends from the proximal end of the first body 56 to the first convex portion 66 to be described later. The locking portion 62 protrudes downward, and the lower end portion of the locking portion 62 possesses a height (dimension in the vertical direction with reference to FIGS. 3A and 3B) that is substantially the same as the height of the second body 58. That is, the lower surface of the locking portion 62 of the first body 56 and the lower surface of the second body 58 lie along a common straight line. The distal end of the first body 56 thus possesses a stepped shape at its distal end portion due to the locking portion 62.

In addition, the first convex portion (protrusion) 66 which protrudes relative to the first connection surface 60 with a predetermined height and possesses an approximately semicircular cross-sectional shape is located between the first connection surface 60 and the locking portion 62. The first concave portion (engaging part) 64 which is recessed relative to the first convex portion 66 with a predetermined depth and possesses an approximately semicircular cross-sectional shape is spaced from and located a predetermined distance toward the distal side (in the direction of arrow B) from the first convex portion 66.

The second body 58 is positioned in the lower portion of the first body 56 (the second body 58 is positioned below the first body 56) and is disposed inside the housing 34 at a position facing the rotary roller 40. The second body 58 is provided with a plurality of second tooth portions 69 which are defined by a series of alternating convex-shaped and concave-shaped elements (a series of alternating projections and recesses) arranged along the axial direction (in the directions of arrows A and B) and disposed on the surface of the second body 58 facing the rotary roller 40. The second body 58 is thus configured as a rack or a rack body.

In addition, the second body 58 has a second connection surface 70 extending along the moving direction (in the directions of arrows A and B) of the displacement body 36 on a surface of the first body 56 side. That is, the second connection surface 70 is positioned on the side of the second body 58 which faces the first body 56. The second connection surface 70 is formed on a planar surface (the second connection surface 70 is a planar surface) and extends from the proximal end of the second body 58 to the second concave portion 74 to be described later. The first connection surface 60 of the first body 56 comes into contact with the second connection surface 70 of the second body 58 when the first body 56 and the second body 58 are combined or brought together to constitute the displacement body 36.

The second concave portion 74 which is recessed relative to the second connection surface 70 with a predetermined depth and possesses an approximately semicircular cross-sectional shape is located in the vicinity of the distal end of the second body 58, and the second concave portion 74 engages the first convex portion 66 of the first body 56. That is, the cross-sectional shape of the second concave portion 74 corresponds to the cross-sectional shape of the first convex portion 66 so that the second concave portion 74 receives the first convex portion 66.

Furthermore, the second convex portion (protrusion) 72 which protrudes relative to the second concave portion 74 with a predetermined height and possesses an approximately semicircular cross-sectional shape is located in the second body 58 at a position spaced from the second concave portion 74 and at a predetermined distance toward the distal side (in the direction of arrow B) from the second concave portion 74. The second convex portion 72 engages the first concave portion 64 of the first body 56. That is, the cross-sectional shape of the second convex portion 72 corresponds to the cross-sectional shape of the first concave portion 64 so that the second convex portion 72 is received in the first concave portion 64.

In addition, the first body 56 and the second body 58 are configured so that the distal end of the second body 58 comes into contact with the locking portion 62 of the first body 56 as shown in FIG. 3A.

That is, the first body 56 and the second body 58 are integrally connected in a state where the relative movement of the two block bodies 56, 58 along the axial direction is restricted by the engagement between the first convex portion 66 and the second concave portion 74 and by the engagement between the first concave portion 64 and the second convex portion 72.

The rotary roller 40, for example, is an annular shape and is rotatably provided in the housing 34 through a rotary shaft, and a side surface of the rotary roller is provided with the gear 38 having a plurality of first tooth portions 80 radially outward and having the rotary shaft as a center and the gear is meshed with the second tooth portion 69 of the displacement body 36. Then, the displacement body 36 is rectilinearly moved along the containing groove 48 due to the rotation of the rotary roller 40.

In a case where a load of not less than a predetermined value is exerted on the second body 58 constituting the displacement body 36 under the rotating action of the rotary roller 40, for example in a situation in which movement of the outer tube body 14 relative to the inner tube body 12 becomes difficult and the operator continues to forcibly rotate the rotary roller 40, the first and second convex portions 66 and 72 and the first and second concave portions 64 and 74 function as releasing mechanisms 82 which release the connected state between the first body 56 and the second body 58 of the displacement body 36 by releasing the engaged state of the convex and concave portions In the operating unit 18 described above, for example, by the rotation of the rotary roller 40 in a predetermined direction (in the direction of arrow C) relative to the housing 34 performed by the operator, the displacement body 36 moves toward the connector 26 side (in the direction of arrow A) along the containing groove 48 inside the housing 34. This is accompanied by movement (retraction) of the outer tube body 14 toward the proximal side (direction of arrow A) of the housing 34. As a result, the stent 16 is released from the distal end of the outer tube body 14.

In contrast, after the stent 16 is released to an intermediate extent, the rotary roller 40 is rotated in the direction opposite to the above-described direction (in the direction of arrow D). By this operation, the displacement body 36 is moved in the direction (in the direction of arrow B) away from the connector 26 along the containing groove 48. This is accompanied by movement (advancement) of the outer tube body 14 toward the distal side (in the direction of arrow B) relative to the inner tube body 12, whereby the stent 16 is again contained in the inside of the outer tube body 14.

The stent delivery system 10 according to this embodiment is configured as described above. Now, the operation and effect of the stent delivery system will be described below.

First, a state is assumed in which the guide wire is inserted into a lumen of a living body (for example, a blood vessel) and the distal end of the guided wire has been put indwelling in a lesion in the lumen of the living body in advance. The operator connects a liquid injector to the connector 26 disposed at the proximal end of the operating unit 18 and injects a liquid such as physiological saline from the liquid injector into the connector 26. As a result, the liquid flows to the distal side of the inner tube body 12 and the outer tube body 14 (in the direction of arrow B). When the liquid reaches the distal end, the liquid is ejected from the distal ends of the inner tube body 12 and the outer tube body 14, whereby priming (air venting) of the inside of the inner tube body 12 and the outer tube body 14 is completed in vitro.

Next, the proximal end of the guide wire exposed in vitro is inserted into the distal end of the inner tube body 12 and passes through the inner tube body 12 into the guide wire lumen. The inner tube body 12 and the outer tube body 14 are gradually advanced together along the guide wire into the lumen of the living body.

After the arrival of the distal end of the outer tube body 14 in the lesion is confirmed by a contrast marker, the displacement body 36 is moved toward the proximal side (in the direction of arrow A) in the housing 34, accompanied by rotation of the gear 38 with the rotary roller 40 rotated in a predetermined direction (in the direction of arrow C). This is accompanied by gradual movement of the outer tube body 14 toward the proximal side of the operating unit 18. As a result, the stent 16 contained in the outer tube body 14 starts being gradually exposed, starting from its distal portion; simultaneously, the stent starts expanding radially outward. Then, the stent 16 comes into the state of being completely exposed from the outer tube body 14, whereby the stent is put indwelling in the lesion in the state of being expanded in the cylindrical shape.

At the time of releasing the stent 16 in the above-mentioned manner, the rotary roller 40 is rotated to gradually move the outer tube body 14 toward the proximal side or in the proximal direction (in the direction of arrow A). However, situations can arise in which, for example, the outer tube body 14 is caught in the lesion in a lumen of a living body so that the movement of the outer tube body 14 toward the proximal side is made difficult.

In such a situation, if the operator continues to forcibly rotate the rotary roller 40 in a predetermined direction, the second body 58, which is in meshing engagement with the gear 38 of the rotary roller 40, is forcibly pulled toward the proximal side (in the direction of arrow A) due to the rotary roller 40. By this operation, the engagement between the second convex portion 72 and the first concave portion 64, and the engagement between the second concave portion 74 and the first convex portion 66, are respectively released. That is, the first convex portion 66 is disengaged from the second concave portion 74, and the second convex portion 72 is disengaged from the first concave portion 64, accompanied by relative movement between the second body 58 and the first body 56, namely relative movement of the second body 58 relative to the first body 56.

In other words, the connected state between the first body 56 and the second body 58, which are connected to each other under the engaging action between the first and second convex portions 66 and 72 and the first and second concave portions 64 and 74, is released. The first and second convex portions 66 and 72, and first and second concave portions 64 and 74, thus form a releasable connection between the first body 56 and the second body 58. The first and second block bodies 56, 58 are connected to each other by this releasable connection that maintains the connection between the first and second block bodies 56, 58 when a load less than a predetermined value is applied to the second body 58 by the operation of the rotary roller 40 so that axial movement of the second body 58 resulting from the operation of the rotary roller 40 is transferred to the first body 56 to axially move the first body 56. On the other hand, the releasable connection releases the connection between the first and second block bodies 56, 58 when a load not less than the predetermined value is applied to the second body 58 by the operation of the rotary roller 40 so that axial movement of the second body 58 resulting from the operation of the rotary roller 40 is not transferred to the first body 56.

Then, as shown in FIG. 3B, only the second body 58 meshed with the gear 38 of the rotary roller 40 is moved toward the proximal side or in the proximal direction (in the direction of arrow A) of the housing 34 relative to the first body 56 along the containing groove 48.

As a result, even if the rotary roller 40 is rotated, the first body 56 is not moved toward the proximal side or in the proximal direction (in the direction of arrow A), so that the outer tube body 14 of which movement has become difficult due to the catching or the like can be reliably prevented from being forcibly pulled proximally. Accordingly, damage to the stent delivery system 10 which might otherwise be caused by forcible movement of the outer tube body 14 through the displacement body 36 can be reliably avoided.

Specifically, when a load (tensile force) of not less than a predetermined value is exerted on the second body 58 through the rotary roller 40 in a state in which movement in the axial direction (in the directions of arrows A and B) of the displacement body 36 is restricted, the second tooth portion 69 of the second body 58 is pulled due to the first tooth portion 80 of the rotary roller 40, whereby the second convex portion 72 of the second body 58 is disengaged from the first concave portion 64 of the first body 56, and the first convex portion 66 of the first body 56 is disengaged from the second concave portion 74 of the second body 58.

The load is appropriately set according to the engagement force between the first convex portion 66 and the second concave portion 74, and the engagement force between the second convex portion 72 and the first concave portion 64. Moreover, the engagement force is set on the basis of a lowest-yield-point part of members in the stent delivery system 10 such as the outer tube body 14, the inner tube body 12, and the like.

As described above, in the first embodiment, the displacement body 36 constituting the operating unit 18 is provided with the first body 56 retaining the outer tube body 14 and the second body 58 which is meshed with the gear 38 of the rotary roller 40 and provided in the lower portion of the first body 56. The second body 58 is thus positioned between the first body 56 and the operating unit 18. With the first convex portion 66 and the first concave portion 64 located between the first connection surface 60 and the locking portion 62 of the first body 56, and with the engagement between the second concave portion 74 and the second convex portion 72 which are located in the vicinity of the distal end of the second body 58, the first body 56 is connected to the second body 58.

Even in a case where the movement of the displacement body 36 and the outer tube body 14 connected to the first body 56 of the displacement body 36 in the axial direction (in the directions of arrows A and B) becomes difficult for some reason, the second body 58 is pulled toward the proximal side (in the direction of arrow A) due to the rotating force transmitted from the rotary roller 40. By this operation, the engagement between the second convex portion 72 and the first concave portion 64, and the engagement between the second concave portion 74 and the first convex portion 66, is released and the second body 58 is relatively moved relative to the first body 56.

As a result, even in a case where the operator continues to forcibly rotate the rotary roller 40, the first body 56 of the displacement body 36 and the outer tube body 14 are prevented from being forcibly pulled due to the rotation of the rotary roller 40. Accordingly, breakage of the lowest-yield-point part in the stent delivery system 10 can be avoided assuredly. Therefore, a situation in which a broken component of the stent delivery system is left in a lumen of a living body can be prevented.

The releasing mechanism 82 is not restricted to being configured to include the first convex portion 66 and the first concave portion 64 which are provided in or as a part of the first body 56 described above, and the second concave portion 74 and the second convex portion 72 which are provided in or as a part of the second body 58 and respectively engaged with the first convex portion 66 and the first concave portion 64. For example, the releasing mechanism of a stent delivery system may be configured according to the releasing mechanism 102 of a stent delivery system 100 shown in FIG. 4A. The releasing mechanism here may be configured such that a concave portion (engaging part) 106 which is recessed relative to the second connection surface 70 with a predetermined depth is located at a distal end of a second body 104, and a convex portion (protrusion) 107 which protrudes relative to the first connection surface 60 with a predetermined height is located at a distal end of a first body 108, whereby the convex portion 107 is engaged relative to the concave portion 106. In the illustrated embodiment, the concave portion or engaging part 106 is a recess, and the convex portion or protrusion 107 is a projection, and the cross-sectional shape of the recess corresponds to the cross-sectional shape of the projection so that the projection fits into the recess so that the projection and the recess engage one another. In the illustrated embodiment, the convex portion or protrusion 107 possesses a square cross-sectional shape and the concave portion or engaging part 106 also possesses a square cross-sectional shape.

The cross-sectional shape of the concave portion 106 and the convex portion 107 is not restricted to the square shape. For example, the cross-sectional shape may be an approximately semicircular shape or a triangular shape.

With the provision of such a configuration, even in a case where the movement of the outer tube body 14 and the displacement body 36 in the axial direction (in the directions of arrows A and B) becomes difficult for some reason and the operator continues to forcibly rotate the rotary roller 40, for example, as shown in FIG. 4B, the second body 104 is pulled toward the proximal side (in the direction of arrow A) due to the rotation of the rotary roller 40 and the engaged state between the concave portion 106 and the convex portion 107 is released. By this operation, the second body 104 is moved toward the proximal side (in the direction of arrow A) relative to the first body 108.

The load (tensile force) exerted on the second body 104 is set on the basis of a lowest-yield-point part of members in the stent delivery system 100 such as the outer tube body 14, the inner tube body 12, and the like.

Accordingly, even in a case where the operator continues to forcibly rotate the rotary roller 40, the displacement body 36 and the outer tube body 14 are prevented from being forcibly pulled due to the rotation of the rotary roller 40. Accordingly, breakage of the lowest-yield-point part in the stent delivery system 100 can be avoided assuredly.

Next, a stent delivery system 150 according to a second embodiment is shown in FIGS. 5A and 5B. Components in this second embodiment of the stent delivery system 150 that are the same as those in the first embodiment of the stent delivery system 10 are identified by common reference numerals and a detailed description of such components is not repeated.

The stent delivery system 150 according to the second embodiment differs from the stent delivery system 10 according to the first embodiment in that an operating unit 152 is provided with a displacement body 158 in which a first body 154 and a second body 156 are connected by coming into contact with each other by a predetermined friction force (the friction force referred herein is maximum static friction force).

As shown in FIGS. 5A and 5B, a first connection surface 160 of the first body 154 is formed in a straight line and in a plane along the axial direction (in the directions of arrows A and B), and a second connection surface 162 of the second body 156 is also formed in a straight line and in a plane along the axial direction (in the directions of arrows A and B).

It is preferable that the first and second connection surfaces 160 and 162 are formed from a material of relatively high friction coefficient such as a rubber, for example. The first and second connection surfaces 160 and 162 themselves are not restricted to the case of being formed from the material of relatively high friction coefficient. For example, members formed from material possessing a relatively high friction coefficient may be mounted on the surfaces of the first and second connection surfaces 160 and 162. In addition, it is also possible that only one (either one) of the first and second connection surfaces 160 and 162 includes material of relatively high friction coefficient.

By bringing the first connection surface 160 of the first body 154 into contact with the second connection surface 162 of the second body 156, the two connection surfaces (and thus the two block bodies 154, 156) are connected in a state that the relative movement of the connection surfaces and block bodies in the axial direction (in the directions of arrows A and B) is restricted by the friction force of the first connection surface 160 and the second connection surface 162.

In other words, the first body 154 and the second body 156 are connected through a releasing mechanism 164 in which the second body 156 can be moved in the axial direction relative to the first body 154 when a load (tensile force along the axial direction) is exerted that is greater than the friction force between the two surfaces.

In the stent delivery system 150 having such a displacement body 158, in a situation where the movement of the outer tube body 14 and the displacement body 158 in the axial direction (in the directions of arrows A and B) becomes difficult for some reason and the operator continues to forcibly rotate the rotary roller 40, the second body 156 meshed with the gear 38 is pulled or urged toward the proximal side or proximal direction (in the direction of arrow A) due to the rotation of the rotary roller 40, and the tensile force of the second body 156 overcomes the friction force between the first connection surface 160 and the second connection surface 162. By this operation, relative movement occurs between the second body 156 and the first body 154. That is, the second body 156 is relatively moved toward the proximal side or proximal direction (in the direction of arrow A) relative to the first body 154. The tensile force is set on the basis of a lowest-yield-point part of members in the stent delivery system 150 such as the outer tube body 14, the inner tube body 12, and the like.

Moreover, as shown in FIG. 5B, with the second body 156 independently moved toward the proximal side (in the direction of arrow A) relative to the first body 154 along a containing groove 48, the rotating force of the rotary roller 40 is prevented from being transmitted to the first body 154 of the displacement body 158 and a situation in which the outer tube body 14 connected to the first body 154 is pulled is prevented.

As a result, even in a situation in which the operator continues to forcibly rotate the rotary roller 40, the first body 154 of the displacement body 158 and the outer tube body 14 are prevented from being forcibly pulled due to the rotation of the rotary roller 40. Accordingly, breakage of the lowest-yield-point part in the stent delivery system 150 can be avoided assuredly. Therefore, a situation in which a broken component of the stent delivery system 150 is left in a lumen of a living body can be prevented.

The operating unit 18 is not restricted to the configuration of rectilinearly moving the displacement body 36 by rotating the rotary roller 40 meshed with the displacement bodies 36 and 158 in the above-described manner. For example, instead of the rotary roller 40, the operating unit can be configured like the operating unit 200 shown in FIG. 6A. The operating unit 200 here includes a protrusion (first tooth portion) 202 in engagement with a groove portion 209 in the second body 58 of a displacement body 36, and a lever (operation body) 204 which is movable with the displacement body 36 relative to the housing 34. As another alternative, the operating unit may be configured as the operating unit 210 shown in FIG. 6B. The operating unit 210 according to this alternative includes a lever (operation body) 212 fixed to the second body 58 of the displacement body 36.

Figure 6A:
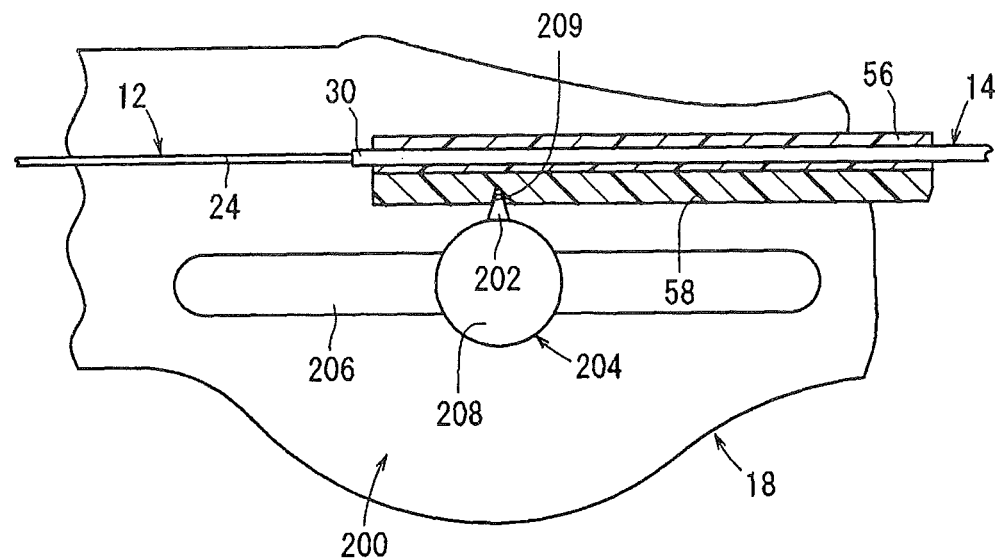
FIG. 6A is an enlarged view showing the vicinity of a displacement body of an operating unit according to a first modified example having a lever instead of a rotary roller.

In the operating unit 200 shown in FIG. 6A, by virtue of the lever 204 that includes a shaft 208 inserted into (positioned in) and passing through a guide hole 206 which opens in the lateral direction of the housing 34 and the protrusion 202 which is located on an end of the shaft 208 and engaged with the groove portion 209 of the second body 58, the operator retains (holds) the shaft 208 of the lever 204 to move the shaft along the guide hole 206. By this operation, the displacement body 36 is moved along the containing groove 48, and the outer tube body 14 is moved toward the proximal side or in the proximal direction (in the direction of arrow A). Therefore, it is possible to release the stent 16.

Figure 6B:
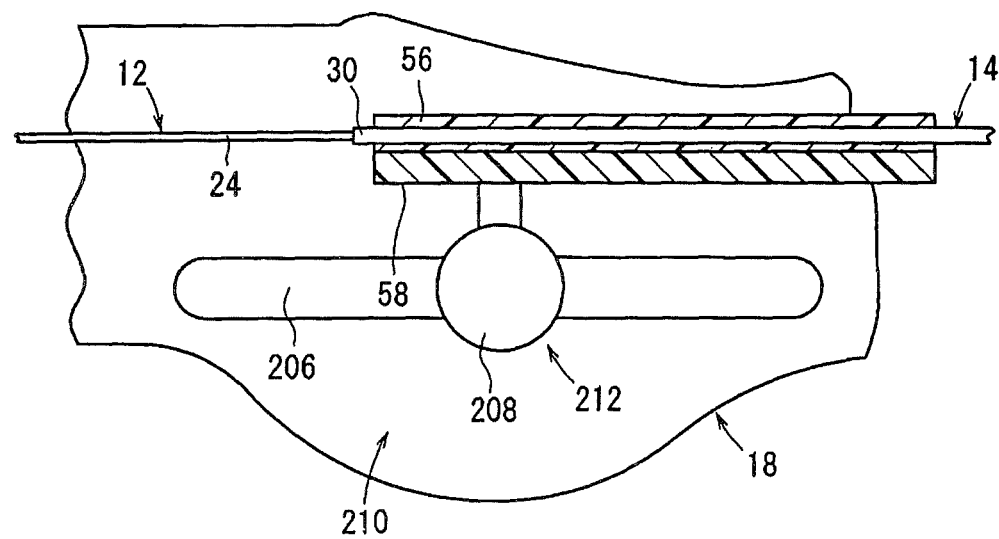
FIG. 6B is an enlarged view showing the vicinity of a displacement body of an operating unit according to a second modified example having a lever instead of the rotary roller.

In the operating unit 210 shown in FIG. 6B, by virtue of the lever 212 fixed to the second body 58, the operator retains (holds) the shaft 208 of the lever 212 to move the shaft along the guide hole 206. By this operation, the displacement body 36 is moved along the containing groove 48 and the outer tube body 14 is moved toward the proximal side or in the proximal direction (in the direction of arrow A). Therefore, it is possible to release the stent 16.

As described above, with the provision of the levers 204 and 212 which can be moved in the horizontal direction relative to the housing 34 to move the levers 204 and 212 with the second body 58, it is possible to move the displacement body 36 and the outer tube body 14 along the axial direction without providing the rotary roller 40 and to release the stent 16. Moreover, in a case where the movement of the outer tube body 14 and the displacement body 36 in the axial direction (in the directions of arrows A and B) becomes difficult for some reason and the operator continues to forcibly move the levers 204 and 212, the second body 58 is pulled toward the proximal side or in the proximal direction (in the direction of arrow A) and the second body 58 is relatively moved toward the proximal side or in the proximal direction (in the direction of arrow A) relative to the first body 56.

The detailed description above describes embodiments of a stent delivery system and method representing examples of the stent delivery system and method disclosed here. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery system comprising:
   an inner tube;
   a stent which is compressed toward a center axis and disposed on a distal side of the inner tube at a time of insertion into a lumen of a living body, and which is restored to its pre-compression shape by expanding outward when put indwelling in the lumen of the living body;
   an outer tube disposed on an outer surface side of the inner tube and possessing a lumen containing the stent, the outer tube being axially movable in a proximal direction relative to the inner tube to release the stent to an exterior of the stent delivery system;
   an operating unit operatively connected to the outer tube to axially move the outer tube relative to the inner tube, the operating unit comprising:
   a housing;
   an operation body operable by an operator;
   a displacement body which is mounted in the housing to axially move relative to the housing, the displacement body including a first block connected to the outer tube and a second block on which a load is exerted due to operation of the operation body by the operator, the second block being connected to the first block; and
   a releasing mechanism by which the connection between the first block and the second block is released so that the second block is moved relative to the first block when a load of not less than a predetermined value is applied to the second block from the operation body.

2. The stent delivery system according to claim 1, wherein the releasing mechanism includes:
   a protrusion on the first block or the second block that protrudes in a direction of movement of the displacement body;
   an engaging part engaged by the protrusion; and
   wherein the second block is moved relative to the first block by release of the engagement between the protrusion and the engaging part due to the load.

3. The stent delivery system according to claim 1, wherein the second block is moved relative to the first block when the load exceeds a friction force between the first block and the second block.

4. The stent delivery system according to claim 1, wherein the first block and the second block are made of different materials.

5. The stent delivery system according to claim 1, wherein the operation body is a rotary body that is rotatably mounted on the housing to rotate relative to the housing, the rotary body including a first tooth portion along an outer circumferential surface of the operation body, and the second block is an axially movable rack that includes a second tooth portion in meshing engagement with the first tooth portion.

6. The stent delivery system according to claim 1, wherein the operation body is a lever which is engaged with or fixed to the second block and moves with the second block relative to the housing.

7. A stent delivery system comprising:
   an outer tube possessing a lumen and an inner surface;
   an inner tube possessing an outer surface, the inner tube being positioned in the lumen of the outer tube so that an annular space exists between the outer surface of the inner tube and the inner surface of the outer tube;
   an operating unit operable by a user to axially move the outer tube in a proximal direction relative to the inner tube;
   a stent positioned in the annular space between the outer surface of the inner tube and the inner surface of the outer tube, the stent being positioned at a distal end portion of the inner tube and being compressed radially inwardly, the stent being outwardly expandable exterior of the stent delivery system to be positioned in a lumen of a living body when the outer tube is axially moved in the proximal direction relative to the inner tube; and
   the operating unit comprising:
   a housing;
   an operation body mounted on the housing and operable by an operator;
   a first block connected to the outer tube so that axial movement of the first block results in the axial movement of the outer tube relative to the inner tube;
   a second block connected to the operation body so that operation of the operation body axially moves the second block; and
   the first block and the second block being connected to each other by a releasable connection that maintains the connection between the first and second blocks when a load less than a predetermined value is applied to the second block by the operation of the operation body to transfer axial movement of the second block resulting from the operation of the operation body to the first block to axially move the first block, and that releases the connection between the first and second blocks when a load not less than a predetermined value is applied to the second block by the operation of the operation body so that axial movement of the second block resulting from the operation of the operation body is not transferred to the first block.

8. The stent delivery system according to claim 7, wherein the releasable connection includes a protrusion positioned in a recess when the first and second blocks are connected, the protrusion being provided on one of the of the first and second blocks, and the recess being provided on the other of the first and second blocks.

9. The stent delivery system according to claim 7, wherein the releasable connection includes a first protrusion on the first block projecting towards the second block, a first recess formed in the first block, a second protrusion on the second block and projecting towards the first block, and a second recess formed in the second block, the first protrusion being positioned in the second recess and the second protrusion being positioned in the first recess when the first and second blocks are connected.

10. The stent delivery system according to claim 7, wherein the operation body includes a tooth portion comprised of a plurality of teeth, and the second block includes a tooth portion comprised of a plurality of teeth, the tooth portion on the operation body being engaged with the tooth portion on the second block.

11. The stent delivery system according to claim 10, wherein the operation body is a rotary body that is rotatably mounted on the housing.

12. The stent delivery system according to claim 7, wherein the operation body is a rotary body that is rotatably mounted on the housing.

13. The stent delivery system according to claim 7, wherein the operation body is an axially movable lever connected to the second block and movable together with the second block relative to the housing.

14. The stent delivery system according to claim 7, wherein the releasable connection includes relatively high friction material on a surface of one of the first and second blocks that contacts the other of the first and second blocks.

15. The stent delivery system according to claim 7, wherein the first block and the second block are made of different materials.

16. The stent delivery system according to claim 7, wherein the releasable connection releases the connection between the first and second blocks when the load applied to the second block by the operation of the operation body exceeds a friction force between the first block and the second block.

17. A method comprising:
positioning a distal end of a stent delivery system in a lumen of a living body, the stent delivery system comprising an outer tube, an inner tube positioned in the outer tube, an inwardly compressed stent between an outer surface of the inner tube and an inner surface of the outer tube, an operation body that is operable by an operator, a first block connected to the outer tube, and a second block connected to the operation body, the second block being connected to the first block;
operating the operation body to axially move the second block in a proximal direction while the distal end of the stent delivery system is in the lumen of the living body;
transferring the axial movement of the second block to the first block by maintaining the connection between the second block and the first block when a load less than a predetermined value is applied to the second block by the operation of the operation body to axially move the first block in a proximal direction, the axial movement of the first block in the proximal direction causing the outer tube to axially move in the proximal direction relative to the inner tube to uncover the stent and allow the stent to outwardly expand in the lumen of the living body; and
not transferring the axial movement of the second block to the first block by releasing the connection between the second block and the first block when a load not less than a predetermined value is applied to the second block by the operation of the operation body so that the axial movement of the second block does not result in axial movement of first block.

18. The method according to claim 17, wherein the second block is connected to the operation body by a tooth portion of the second block engaging a tooth portion of the operation body.

19. The method according to claim 17, wherein the releasing of the connection between the second block and the first block comprises a protrusion which is positioned in a recess being disengaged from the recess, the protrusion being provided on one of the first and second blocks, and the recess being provided on the other of the first and second blocks.

20. The method according to claim 17, wherein the releasing of the connection between the second block and the first block occurs when the load applied to the second block by the operation of the operation body exceeds a friction force between the first block and the second block.

* * * * *